United States Patent [19]

Mezei et al.

[11] Patent Number: 5,888,536
[45] Date of Patent: Mar. 30, 1999

[54] LIPOSOME COMPOSITION CONTAINING SELEGILIN

[75] Inventors: Michael Mezei, Vancouver, Canada; Jozsef Gaal, Budapest; Gabor Szekacs, Godollo, both of Hungary; Gyula Szebeni, Budapest; Katalin Marmarosi, Biatorbagy, both of Hungary; Kalman Magyar; Jozsef Lengyel, both of Budapest, Hungary; Istvan Szatmari; Agnes Turi, both of Budapest, Hungary

[73] Assignee: Chinoin Ltd., Budapest, Hungary

[21] Appl. No.: 817,433

[22] PCT Filed: Oct. 20, 1995

[86] PCT No.: PCT/HU95/00052

§ 371 Date: Aug. 5, 1997

§ 102(e) Date: Aug. 5, 1997

[87] PCT Pub. No.: WO96/12472

PCT Pub. Date: May 2, 1996

[30] Foreign Application Priority Data

Oct. 24, 1994 [HU] Hungary .................. P9403073

[51] Int. Cl.$^6$ ..................... A61K 9/127; A61K 31/135; A61K 31/13
[52] U.S. Cl. .................. 424/450; 514/647; 514/654; 514/661
[58] Field of Search ............ 424/450; 514/647, 514/654, 661

[56] References Cited

U.S. PATENT DOCUMENTS

| | | |
|---|---|---|
| 4,089,801 | 5/1978 | Schneider ................ 252/316 |
| 4,485,054 | 11/1984 | Mezei et al. ............. 264/4.6 |
| 4,761,288 | 8/1988 | Mezei .................. 424/450 |
| 4,937,078 | 6/1990 | Mezei et al. ............. 424/450 |

OTHER PUBLICATIONS

Windholz et al., *T6 Merck Index*, 10th Ed. p. 419 abstract No. 2876 (Selegilin).

*Primary Examiner*—Kevin E. Weddington
*Attorney, Agent, or Firm*—Birch, Stewart, Kolasch & Birch, LLP

[57] ABSTRACT

This invention provides liposomic composition, containing as active ingredient (−)-N-α-dimethyl-N-(2-propynylphenylethylamine) (selegilin) and/or salt thereof. This composition contains: 0.1–40% by weight of selegilin and/or a salt thereof, 2 to 40% by weight of lipids, preferably phospholipids, 0 to 10% by weight of cholesterol, 0 to 20% by weight of an alcohol, 0 to 25% by weight of a glycol, 0 to 3% by weight of an antioxidant, 0 to 3% by weight of a preserving agent, 0 to 2% by weight of a viscosity influencing agent, 0 to 50% by weight of cyclodextrin or a cyclodextrin derivative and 30 to 90% by weight of water. This invention relates to pharmaceutical composition, containing the liposomic composition described and if desired, usual filling and diluting agents and other auxiliaries, preferably in oral, parenteral or transdermal form. This invention provides the process for the preparation of liposomic compositions containing selegilin and/or salt thereof. Accordingly liposomic composition of this invention may be administered for the treatment of Alzheimeir's disease, Parkinson's disease, depression, stroke, motion sickness or myelitis.

14 Claims, 6 Drawing Sheets

LIPOSOME COMPOSITION CONTAINING SELEGILIN

This appln. is a 371 of PCT/HU95/00052, filed Oct. 20, 1995.

The invention relates to liposomic compositions containing as active ingredient selegilin (−)-(N-α-dimethyl-N-(2-propynylphenylethylaniine) and/or a salt thereof. Further, the invention relates to their preparation, pharmaceutical compositions containing them and their therapeutical use.

Nowadays a great number of liposomic compositions and processes for their preparation is known in the art.

Such compositions are, as a matter of fact, "drug delivery systems" (DDS), as described by G. Gregoriadis et al (Receptor-mediated targeting of drugs, Plenum Press, New York. 243–266, 1980). They contain the active ingredient similarly to encapsulated status in one or more lamellar membranes comprising lipids, i.e. in liposomes. The good absorption and biodisposition of the active ingredient(s) can be influenced among others by the composition and method of preparation of the liposomes so that it can deliver the active ingredient into a specified area. In the liposomic compositions the active ingredient is encompassed by one or more lipid lamella(s) which also serve as a carrier of the active ingredient.

Multilamellar lipid vehicles (MLV) were first prepared and described by Bangham et al (J. Mol. Biol. 13, 238–252, 1965).When biologically active substances are encapsulated in small, unilamillar lipid vesicles, water-soluble substances can be encapsulated by poor efficiency due to the small volume of water encapsulated into the SUV (small unilamellar lipid vesicles) (U.S. Pat. No. 4,089,801).

Unilamellar lipid vesicles were prepared by other methods, i.e. by injecting ethanol [S. Batzri and E. D. Korn: Biochem. Biophys. Acta. 298: 1015–1019, (1973)] or ether [D. Deamer and A. D. Bangham: Biochem. Biophys. Acta 443, 629–634, (1976)] so that the solution of lipids in an organic solvent was injected quickly into a buffer solution and thus unilamellar liposomes were formed spontaneously. The method is rapid and generally used but results in diluted liposomic preparations and poor encapsulating effectivity.

Unilamellar liposomes can be formed also by the so-called detergent removing system [H. G. Weder and O. Zumbuehl: Liposome Technology, ed. G. Gregoriadis, CRC Press Inc., Boca Raton, Fla., Vol. 1. Ch 7, pp. 79–107, (1984)], in the course of which the lipids and other substances are dissolved together with detergents and then the detergents are removed by dialysis.

Multilamellar liposoinic encapsulation is carried out according to U.S. Pat. No. 4,234,871 (Papahadjopoulos) by the so-called reverse phase evaporation (REV) technique and according to U.S. Pat. No. 4,016,100 (Suzuki) by lyophilizing the aqueous-lipidic dispersion of lipids and the biologically active substance.

In the published patent specification No. WO 93/20934 the preparation of a stable, aqueous liposomic suspension is disclosed which can be stored for 6 months at 40° C.

In the course of the preparation of the above liposomic compositions the dispersion of the lipids and the aqueous phase is carried out in contact reactions on an inert solid material, in most cases on glass pearls [U.S. Pat. No. 4,485,054].

According to U.S. Pat. No. 4,761,288 which is expressly incorporated herein by reference, multiphase systems are prepared for improving the absorption of the biologically active substances having poor water-solubility, which contain the active ingredient in super-saturated solution form, in solid form and encapsulated in multilamellar lipid vesicles. The vesicles, the solution and the solid form of the biologically active compound are dispersed in a hydrocolloidal gel. The hydrocolloidal gel is prepared by utilizing the method for preparing multilamellar lipid vesicles described in U.S. Pat. No. 4,485,054 expressly incorporated herein by reference. Thus, liposomic compositions can be prepared, in which the active ingredient is present in higher concentrations than could be expected on the basis of its water- and/or liposolubility.

In U.S. Pat. No. 4,937,078 liposomic compositions of locally applied anesthetic and analgesic active ingredients are disclosed. It was found that locally applied active ingredients are more effective in liposomal encapsulated state than the usual ointment, cream or liquid compositions. The liposoma formation itself has been carried out as disclosed in U.S. Pat. Nos. 4,485,054 and 4,761,288.

The preparation of all the liposomic compositions has been directed to active ingredients having poor water-solubility, first of all for increasing the absorbability and the local concentration and/or for scheduled absorption.

Our invention relates to the preparation of liposomic compositions from selegilin or its salts, which are well-soluble in water and solvents (1 g/3 ml in water, 1 g/5 ml in chloroform or 1 g/3 ml in methanol), further to their oral, parenteral or local therapeutical applications, optionally in transdermal, controlled release compositions.

Selegilin is a known pharmaceutical composition, widely marketed under the name of Jumex, Deprenyl, Eldepryl or L-Deprenyl, being widely effective, e.g. in the treatment of tuberculosis or immune modulation [A. Dow: The Deprenyl Story, Toronto: Stoddart (1990); Inhibitors of Monoamine Oxidase B, Edited by I. Szelenyi, Birkhauser Verlag, Basel-Boston-Berlin, 237–358 (1993)]. One of its important effects is its antidepressant and psychostimulating and MAO-inhibiting effect, more closely, its selective MAO-B inhibiting effect. Several processes are known for its preparation, see e.g. Hungarian patent specifications Nos. 151,090, 154, 655 and 187,775. L-Deprenyl was approved by the FDA in 1989 as an agent for the treatment of Parkinson's disease.

The liposomic composition according to the present invention contains preferably 0.1 to 40% by weight of selegilin (−)-[N-α-dimethyl-N-(2-propynylphenylethylamine)] and/or a salt thereof, 2 to 40% by weight of lipids, preferably phospholipids, 0 to 10% by weight of cholesterol, 0 to 20% by weight of an alcohol, 0 to 25% by weight of a glycol, 0 to 3% by weight of an antioxidant, 0 to 3% by weight of a preserving agent, 0 to 2% by weight of a viscosity influencing agent, 0 to 50% by weight of cyclodextrin or a cyclodextrin derivative and 30 to 90% by weight of water.

The liposomic composition according to the present invention contains preferably 0.1 to 20, more preferably 0.1 to 10% by weight of selegilin and/or a salt thereof and at least 10% by weight of this quantity in uni- and/or multi-lanellar lipid vesicle and the remainder quantity necessary to 100% by weight in free state and/or as a saturated solution. The liposomic composition according to the invention contains as a lipid preferably a phospholipid, preferably phosphatidyl choline and/or lisophosphatidyl-choline and/or phosphatidyl serine and/or phosphatidyl ethanolamine and/or phosphatidyl inositole; as an alcohol preferably, ethanol or isopropanol; as a glycol preferably a propylene glycol or polyethylene glycol; as an antioxidant preferably tocopherol or BHA (butylhydroxyanisole): as a preserving agent preferably germaben (International Specialty Product, Vienna, Austria): as a viscosity influencing agent preferably a hydrocarbon or a cellulose derivative, preferably carbopol (Carbomer, Goodrich, Cleveland); and as a cyclodextrin and/or a cyclodextrin derivative preferably α-, β- or γ-cyclodextrin a water-soluble cyclodextrin polymer, a methylated, hydroxypropylated or succinylmethylated cyclodextrin derivative or any mixture thereof.

The compositions according to the invention may contain the liposomic composition, if desired, together with filling, diluting or auxiliary agents generally used. It can be administered preferably orally, parenterally or in transdermal form. When preparing a transdermal formulation, the liposomic composition may be applied on a carrier surface, preferably on a foil, film or plaster.

The liposomic compositions can be prepared as disclosed in the U.S. Pat. Nos. 4,485,054 and 4,761,288, the organic solvent is evaporated from an organic solvent mixture containing liposoluble components, comprising at least one lipid, and selegilin, then combined with an aqueous solution of the water-soluble components under stirring. As an organic solvent mixture preferably a mixture of chloroform and methanol is used.

The liposomic compositions according to the invention can preferably be used for the treatment of Alzheimer's disease, Parkinson's disease, depression, stroke, motion sickness or myelitis.

The liposomic composition itself contains the active ingredient in a multiphase, unilamellar and/or multilamellar vesicle, in free state and in its saturated solution, i.e. it is a multiphase liposomic drug delivery system. The thus-obtained liposomic system is stable and can freely be diluted with water. Its rheological features can be varied from the dilute-liquid to the gelatinous state.

From pharmacological point of view we aimed at preparing selegilin containing liposomic compositions which are controlled release drug delivery systems and thus enable the administration of exact doses during transderinal treatment even at "once a week" dosage regime. The mode of administration and the dose depends, among others, on the disease to be treated (Alzheimer's disease, Parkinson's disease, depression, stroke, motion sickness or myelitis), on its severity, the general state of the patient etc.

The in vivo pharmacological and pharmacokinetical examination of the liposomic compositions has been carried out on albino guinea-pigs weighing 300 to 350 g (Charless-River line, SPF: specific phatogene free quality) by local treatment, on groups comprising three animals selected at random for the test animals.

The second phase of the experiments has been carried out on pigs of 20 to 22 kg, by treating three animals by a single dose of one of the formulas.

The animals were kept separately in cages on waste wood litter at an average temperature of 23° C., fed with the same fodder and watered.

As test compositions the products according to Examples 1, 2, 3 and 6 were used.

The liposomic Deprenyl preparations were applied on the unhaired back (guinea-pigs) or neck skin (pigs) on a surface of 1.5×15 and 3×3 cm², respectively, and after drying for some minutes fastened by Tegaderm (produced by 3M, USA). As a control, pigs were treated orally with selegilin-tablets once a day.

During the evaluation the MAO-inhibition was measured in the blood, the brain, liver and intestines, further the concentration of the active ingredient and its metabolites in the blood. The accumulation of the active ingredient and its metabolites in the different organs of the pigs (blood, brain, heart, liver, kidney, lungs and spleen) was examined after a treatment with selegilin-liposomes marked with $^3$H-isotope by radioactive detection technique.

Blood samples were taken for determining the serum concentrations before treatment and then 6, 24, 48, 72, 96, 120, 144 and 168 hours after administration. The amount of selegilin and its metabolites, further the MAO-B activity of the platelets were measured.

The Tagederm fasteners were removed after 6 hours and from the alcoholic extract the remaining, not absorbed amount of selegilin was measured.

After finishing the experiments the MAO-activity was also determined from the isolated brain. liver and intestines of the killed animals. By determining the activity of the MAO-A and MAO-B enzymes the selectivity of the enzyme inhibition was also examined.

The combined concentration of Deprenyl and its metabolites was measured in the blood and in the isolated brain, lungs, spleen, liver, heart, stomach, small and large intestines and kidney of the killed animals, as well as on the skin surface where the liposomic treatment was carried out. The blood samples were taken at determined intervals from the canthus of the guinea-pigs and from the big throat-vain of the pigs.

At the end of the seventh day the guinea-pigs were killed and a blood sample was taken immediately directly from the heart. In the case of the pigs blood samples were taken before killing as described above.

The removed organs and tissues were measured and homogenized with a 4fold volume of physiologic sodium-chloride solution. The 3×5 μl aliquots were pipetted into cuvettas containing 2 ml of Solune 350 and 0.5 ml of isopropanol. The samples are further processed as described above for the blood samples.

The radioactivity of the organs is determined by liquid scintillation counting, the data obtained gives the total quantity of the measurable Deprenyl and the metabolites.

The amount of the drug remaining on the parafilm and the Tegaderm is also determined by radioactive technique.

The specific radioactivity is determined from the aliquot samples of the original liposomic preparations, which were used for calculating the values relating to the organs and tissues.

The MAO-activity in the brain was determined by the method of Wurtman and Axelrod [Biochem. Pharmacol. 12, 1414–1419 (1963)] and the protein content of the homogenizates was determined by the method of Lowry et al [J. Biol. Chem. 193, 265–275 (1951)].

The MAO-activity of the platelets was examined by the method of Willberg and Oreland [Med. Biol. 54, 137–144 (1976)].

The concentration of selegilin and out of its metabolites that of amphetamine, methamphetamine and dezmethyl-selegillin was determined by gas chromatography.

The biological pharmacological results are elucidated in the following figures.

Figure 1:
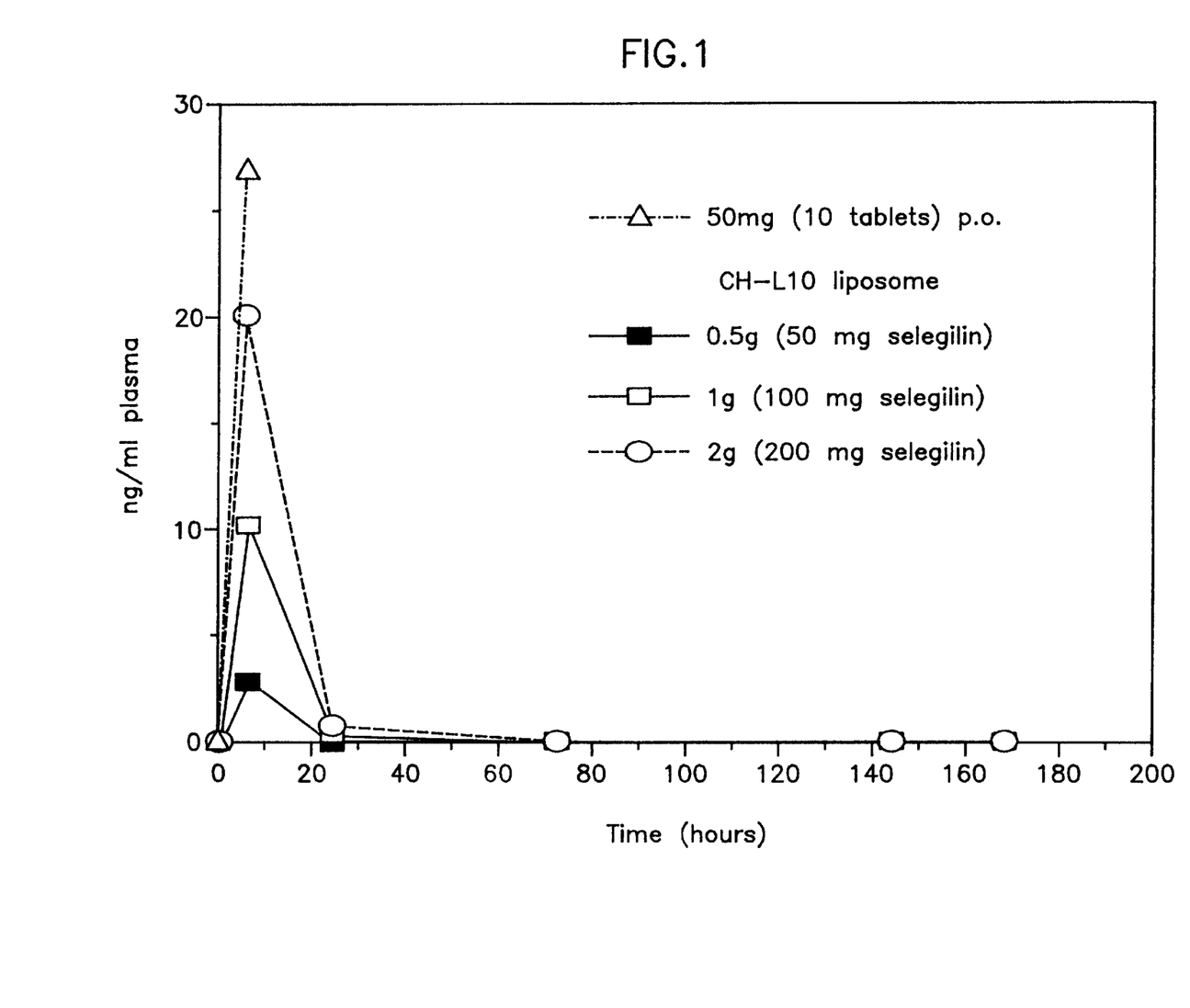
FIG. 1. Average methamphetamine plasma levels (±SD, n=3) in pig, after oral and transdermal (−)Deprenyl (CHL-10) treatment FIG. 2. Average methamphetamine plasma levels (±SD, n=3) in pig after transdermal treatment with a liposomic composition containing (−)Deprenyl FIG. 3. MAO-B inhibition of the platelet after the transdermal administration of a liposomic composition (CHL-10) and the oral administration of traditional tablets FIG. 4. MAO-B inhibition in the platelet 168 hours after the transdermal administration of a multilamellar liposomic composition FIG. 5. MAO inhibition in the brain, liver and small intestines 168 hours after the transdermal administration of the CHL-2 liposomic composition FIG. 6. MAO inhibition in the brain and the liver 168 hours after the transderrnal administration of the liposomic compositions FIG. 7. Serum concentrations calculated from radioactivity (unchanged substance and metabolite) after the transdermal administration of different doses of composition CHL-2
Figure 2:
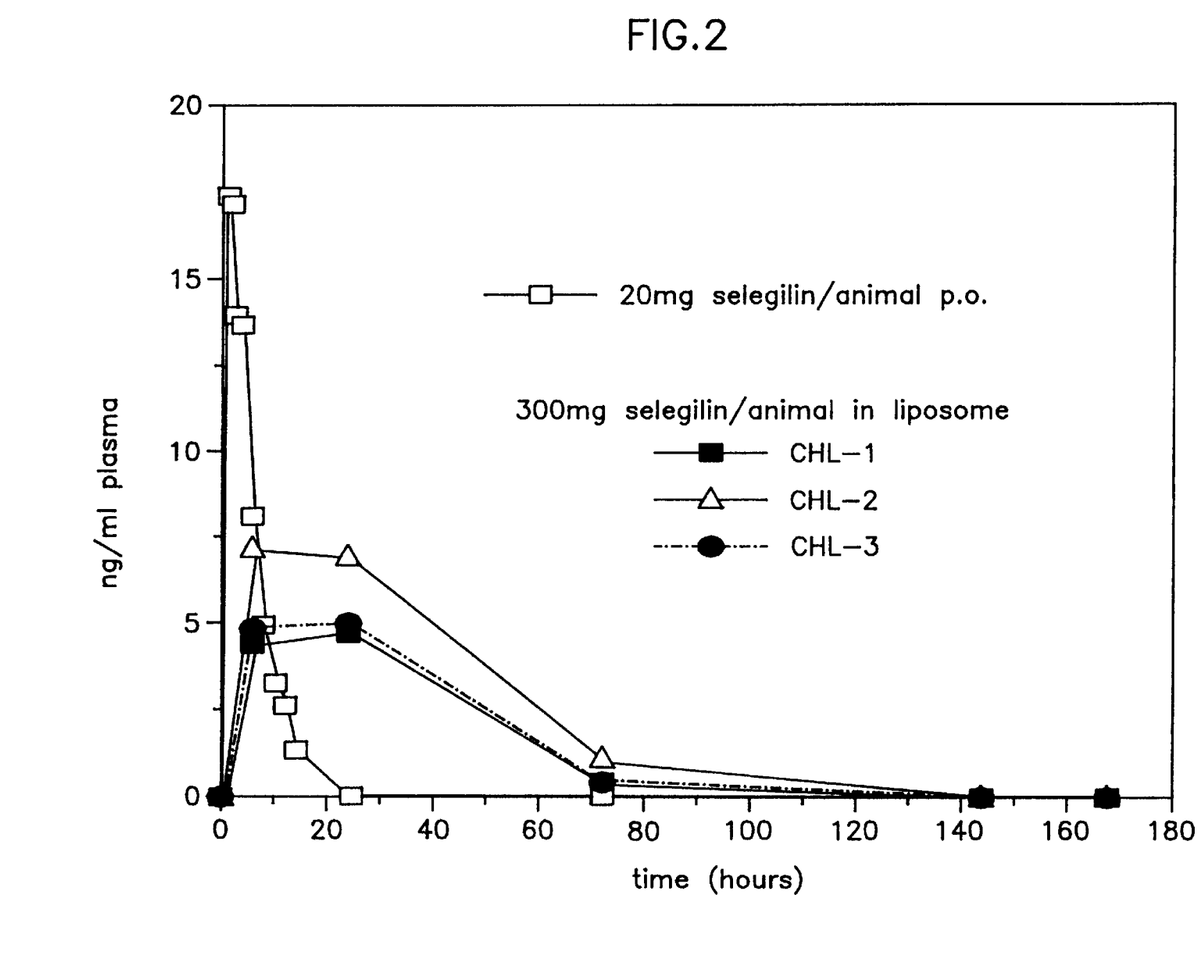

FIGS. 1 and 2 show the blood level data of the main metabolite of selegilin, i.e. methamphetamine. after applying once the selegilin-liposomic composition transdermally.

When applying the mainly unilamellar liposomic composition of smaller vesicle distribution according to Example 6 the absorption and the metabolism is rapid, a dose-depending blood level was measured for 24 hours (FIG. 1).

The mainly multilamellar liposomes of falling under the greater particle size distribution range (Examples 1 to 3) produce a slow, retarded blood level, the components having a low number of lamellas ensure a relatively high blood level for 72 hours and the multilamellar composition ensures a measurable blood level even after 168 hours (FIG. 2).

Figure 3:
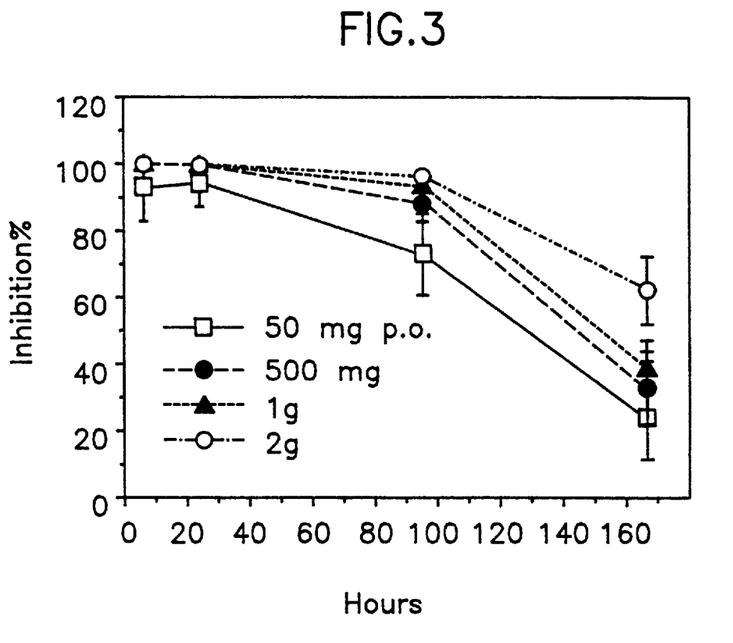
Figure 4:
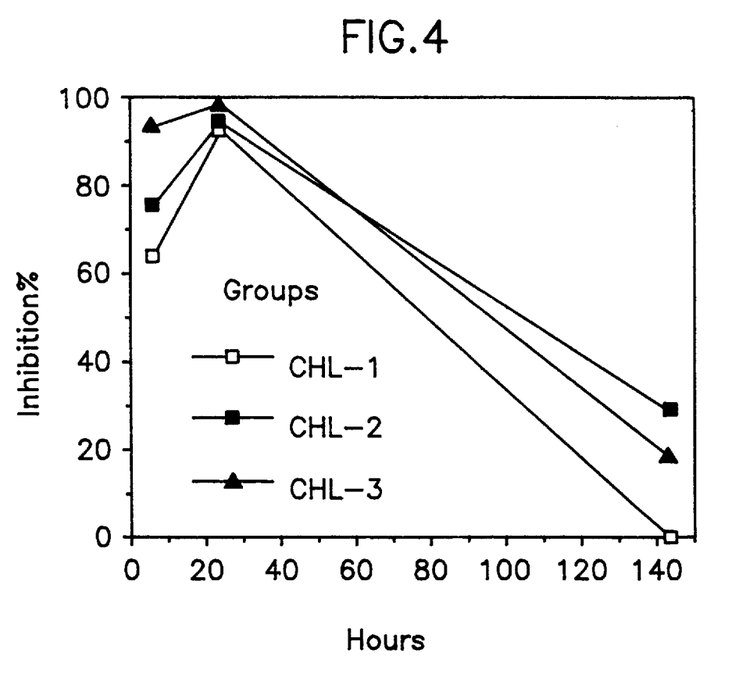
Figure 5:
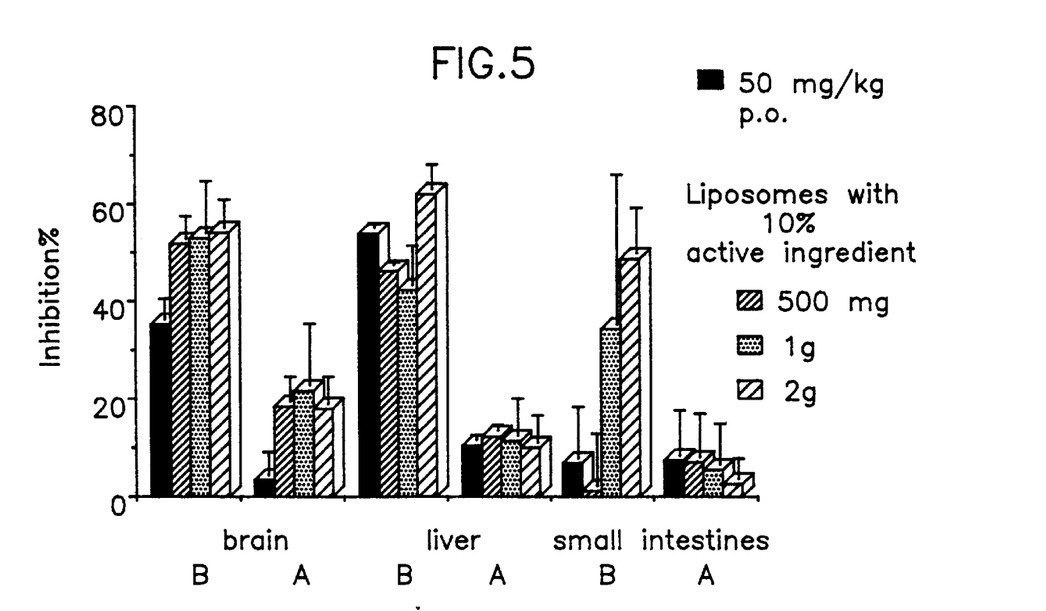
Figure 6:
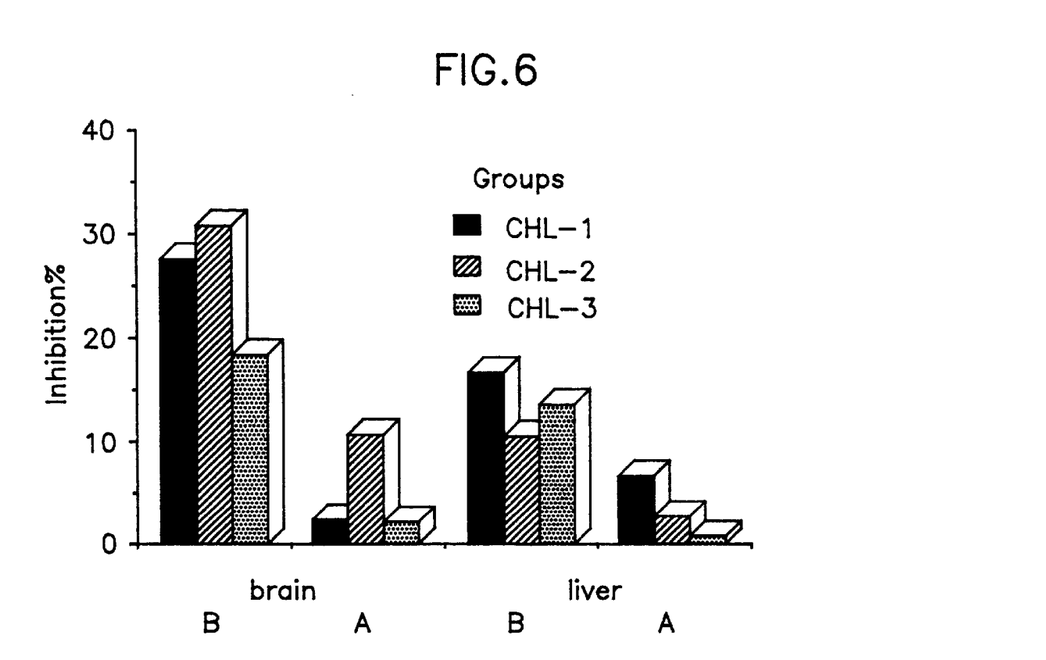

In the case of the same compositions it can also be stated that the composition ensuring a rapid absorption produced a stable MAO-inhibition, while the slow absorption causes a relatively rapidly regenerating inhibition in the blood (FIGS. 3 and 4). Similar data were measured in the brain, too (FIGS. 5 and 6).

Figure 7:
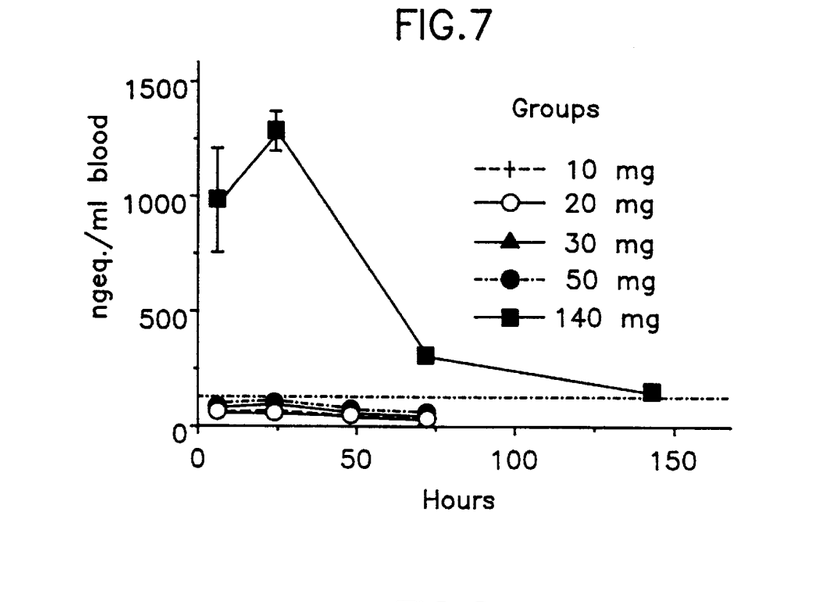
Figure 8:
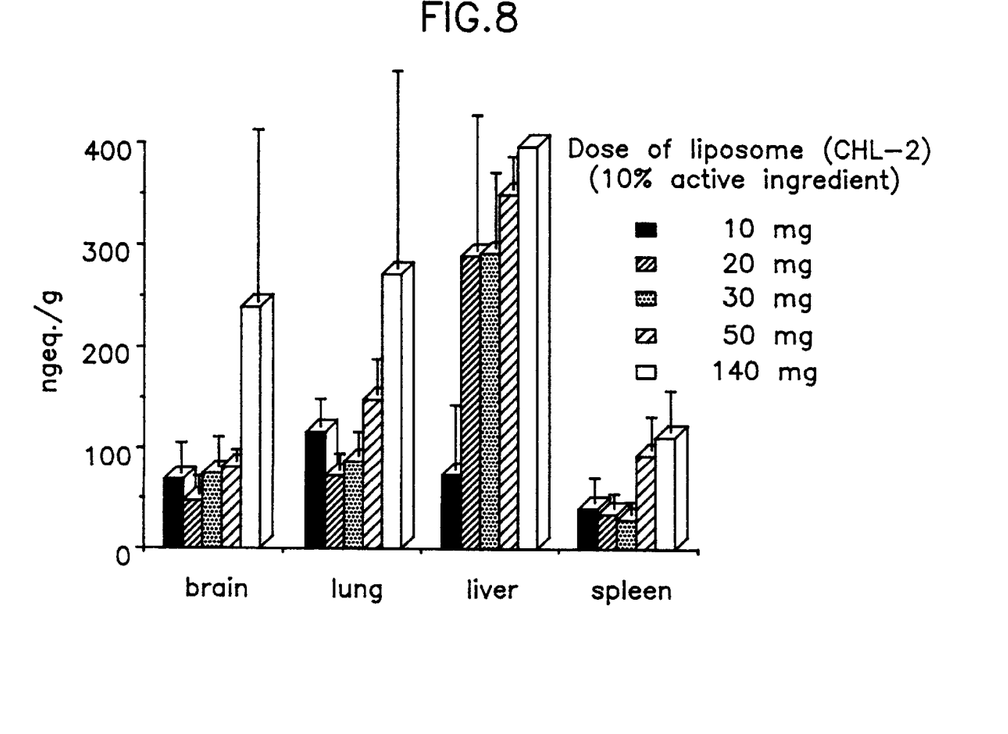
FIG. 8. Concentration of a radioactive substance (selegilin+metabolites) 168 hours after the transdermal administration of the composition CHL-2
Figure 9:
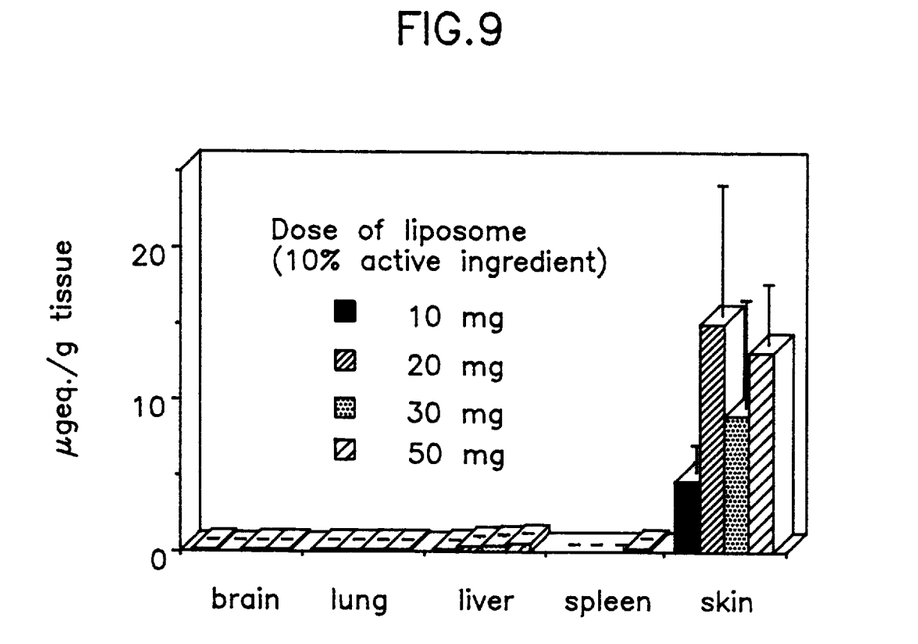
FIG. 9. The radioactivity of the different organs of guineapigs and that of the site application 168 hours after the transdermal administration of the composition CHL-2

Similar blood levels were measured in the radioactive tests on guinea-pigs (unchanged selegilin and metabolites thereof together) (FIG. 7). In the case of liposomes of slow absorption significant levels could be measured in the organs dispite of the blood level decrease by the 168th hour, both in the brain being important as regards the effect, both in the liver playing and important role in the metabolism and in all lipophilic organs (FIG. 8 and Table 1). These organs can serve as a depot releasing the active ingredient later. The intestines contain a relatively small amount of the substance, thus supporting the inhibition data and the lack of MAO-A inhibition (FIG. 5). FIG. 9 (Table 1) compares the levels measured in the organs with the quantity of the substances accumulated in the skin. It can well be seen that although significant, above 10 ng/g values can be measured in the organs, which are higher than the known postmortem human data (broken line in the Figure), there are still significant reserves in the skin which may ensure an active ingredient supply for a long time. The different doses, 10 and 140 mg, cause a significantly higher difference in the blood (about a 100 fold) than in the brain (only 2 to 3 fold) (comp. FIGS. 7 and 8).

The examinations support the following advantages of the selegilin-containing liposomic compositions:

The active ingredient avoids the gastro-intestine tracts, thus causing a significant decrease in the inhibition of the MAO-A enzyme concentrated there and playing an important role in the metabolism of the tiramine because it does not meet the active ingredient.

By any other route of administration than oral (intravenous, intramuscular, eye drop, nasal spray, evaporator etc), the active ingredient avoids the vena portae and thus the first pass metabolism. Thus, it causes higher selegilin and decreased metabolite levels, the MAO-A-inhibition decreases. It is less probable that "cheese"-effect occurs. Higher doses can be applied without side-effects and e.g. antidepressant indication may widen. The metabolites are stimulating and cause sleeplessness, their lower level means the decrease of the side effects.

When administered transdermally, the skin stores the quantity of the active ingredient necessary for the continuous absorption in a manner not limiting its function.

The absorption of the liposomic composition (depending on the formulation) takes about 1 to 20 minutes, thereafter any fastening or coverage (patch, Tegaderrn) is superfluous, it cannot be washed, thus does not hinder washing, its removal cannot be feared even in dementia. By changing the formulation (composition or particle size) an optimal retardation (1 day, 1 week, several weeks) can be achieved. By changing the ratio of the encapsulated and the free active ingredient a stable ingredient:metabolite ratio can be achieved which is optimal as regards the neuroprotective and neurorescue effects.

The invention is elucidated by the following non-limiting examples.

EXAMPLES 1 to 6

Preparation of Liposomic Deprenyl Compositions

Example 1

20 g of Phospholipon 90-G (unsaturated phospholipid) and 10 g of selegilin hydrochloride are dissolved in a round-bottomed flask in 20 ml of a 2:1 mixture of chloroform and methanol at a temperature of 40° C. 100 g of small glass pearls are added to the solution. The solvent is evaporated in vacuo in Rotavapor and during this procedure thin film is formed on the wall of the glass flask and the surface of the glass pearls. 70 g of a 1:3 mixture of ethanol and water heated to 40° C. is added thereto. The content of the flask is well shaken and then further shaken at a medium speed of 200 rotation/minute for 30 minutes at 35° C. The glass pearls are filtered off through a Buichner funnel without filter paper. The filtrate is allowed to stand for an hour at room temperature to allow the liposomic system to form. The formation of liposomes is confirmed by optical microscope examination. The total weight of this (CH-L-1) liposomal product is 100 g.

The liposomic structure is proved by the microscopic examination and the measurement of particle size distribution.

Example 2

A liposomic selegilin composition is prepared as described in Example 1 with the difference that as phospholipid Phospholipon 90-H is used. Also 100 g of the product (CH-L-2) are obtained. Its liposomic structure is proved by the microscopic examination and the measurement of particle size distribution.

Example 3

One proceeds as described in Example 1 with the difference that phospholipid in an amount less by 1 g and cholesterol in amount of 1 g are dissolved in the organic solvent mixture. The product obtained is named (CH-L-3).

Example 4

One proceeds as described in Example 1 with the difference that 20 g of selegilin and 30 g of phospholipid were used. The 118 g product is proved to be a liposomic composition by its microscopic examination and the measurement of particle size distribution.

Example 5

One proceeds as described in Example 2 but 30 g of selegilin, 40 g of a phospholipid and 40 ml of a mixture of chloroform and methanol were used. 135 g of a product are obtained which proved to be a liposomic composition by its microscopic examination and the measurement of particle size distribution.

Example 6

One proceeds as described in Example 1 with the difference that 16 g of Phospholipon 90-H, 4 g of cholesterol, 10 g of selegilin hydrochloride, 50 g of distilled water and 5 g of propylene glycol were used and the shaking was carried out at a speed of 250 rotation/minute.

The product obtained (CH-L-10) proved to be a liposomic composition by its microscopic examination and the measurement of particle size distribution. Its average particle size is smaller than that of the products obtained according to Examples 1 to 5.

TABLE 1

The radioactivity content of different organs (in μgeq/g tissue) of quinea pigs one week after 140 mg of liposome-formulated ³H deprenyl (containing 14 mg deprenyl. aprox. 42 mg/kg) The first (shaded) data are measured after 24 hours, not included in the mean value.)

| | Measured radioactivity (ugeq/g) | | | | | | | | |
|---|---|---|---|---|---|---|---|---|---|
| | CHL-1 | | | CHL-2 | | | CHL-3 | | |
| organs | value | mean | S.D | value | mean | S.D | value | mean | S.D |
| brain | 0.942 | | | 0.416 | | | 0.168 | | |
| | 0.123 | 0.096 | 0.038 | 0.217 | 0.238 | 0.169 | 0.335 | 0.259 | 0.084 |
| | 0.069 | | | 0.080 | | | 0.273 | | |
| lung | 2.370 | | | 0.150 | | | 0.285 | | |
| | 0.252 | 0.220 | 0.045 | 0.496 | 0.271 | 0.195 | 1.016 | 0.599 | 0.376 |
| | 0.188 | | | 0.167 | | | 0.497 | | |
| heart | 3.572 | | | 0.555 | | | 0.447 | | |
| | 0.160 | 0.175 | 0.021 | 0.855 | 0.550 | 0.308 | 2.074 | 0.987 | 0.941 |
| | 0.191 | | | 0.239 | | | 0.441 | | |
| spleen | | | | 0.630 | | | 0.367 | | |
| | 0.199 | | | 0.376 | 0.395 | 0.226 | 0.707 | 0.615 | 0.217 |
| | 0.191 | 0.195 | 0.005 | 0.179 | | | 0.770 | | |
| liver | 1.065 | | | 0.143 | | | 0.102 | | |
| | 0.052 | 0.052 | 0.0007 | 0.121 | 0.110 | 0.040 | 0.124 | 0.126 | 0.026 |
| | 0.053 | | | 0.065 | | | 0.153 | | |
| kindney | 1.704 | | | 0.417 | | | 0.353 | | |
| | 0.229 | 0.198 | 0.043 | 0.330 | 0.308 | 0.121 | 0.421 | 0.422 | 0.069 |
| | 0.167 | | | 0.178 | | | 0.491 | | |
| stomach | 0.975 | | | 0.019 | | | 0.063 | | |
| | 0.018 | 0.021 | 0.004 | 0.030 | 0.029 | 0.010 | 0.037 | 0.054 | 0.015 |
| | 0.024 | | | 0.039 | | | 0.063 | | |
| smal int. | 0.183 | | | 0.021 | | | 0.025 | | |
| | 0.016 | 0.012 | 0.004 | 0.021 | 0.017 | 0.007 | 0.015 | 0.018 | 0.006 |
| | 0.009 | | | 0.009 | | | 0.015 | | |
| colon | 0.164 | | | 0.031 | | | 0.014 | | |
| | 0.005 | 0.012 | 0.009 | 0.034 | 0.027 | 0.010 | 0.008 | 0.013 | 0.004 |
| | 0.019 | | | 0.016 | | | 0.016 | | |
| skin | 80.493 | | | 53.521 | | | 22.550 | | |
| | 5.856 | 51.798 | 64.972 | 25.633 | 62.160 | 41.527 | 19.081 | 19.410 | 2.989 |
| | 97.741 | | | 107.327 | | | 16.599 | | |

We claim:

1. A liposome composition comprising an effective amount of selegilin which is (−)-N-α-dimethyl-N-(2-propynylphenylethylamine) or a pharmaceutically acceptable salt thereof or mixtures thereof; and a liposome carrier.

2. A liposome composition comprising 0.1–40% by weight of selegilin which is (−)-N-α-dimethyl-N-(2-propynylphenylethylamine) or a pharmaceutically acceptable salt thereof, or mixtures thereof, 2 to 40% by weight of lipids, 0 to 10% by weight of cholesterol, 0 to 20% by weight of an alcohol, 0 to 25% by weight of a glycol, 0 to 3% by weight of an antioxidant, 0 to 3% by weight of a preserving agent, 0 to 2% by weight of a viscosity influencing agent, 0 to 50% by weight of cyclodextrin or a cyclodextrin derivative, and 30 to 90% by weight of water.

3. The liposome composition as claimed in claims 1 or 2, comprising 0.1 to 20% by weight of selegilin or a pharmaceutically acceptable salt thereof, or mixtures thereof.

4. The composition as claimed in claim 2, wherein said lipid is a phospholipid.

5. The composition as claimed in claim 2, wherein said alcohol is ethanol or isopropanol; said glycol is a propylene glycol or polyethylene glycol; said antioxidant is a tocopherol or butylhydroxyanisole; said preserving agent is germaben; and said viscosity influencing agent is carbapol.

6. The composition as claimed in claim 2, wherein said cyclodextrin and/or a cyclodextrin derivative is selected from the group consisting of $\alpha$-, $\beta$-, $\gamma$-cyclodextrin, a water-soluble cyclodextrin polymer, a methylated, hydroxypropylated and succinylmethylated cyclodextrin derivative, or mixtures thereof.

7. A pharmaceutical composition comprising the liposome composition according to claims 1 or 2, and a pharmaceutically acceptable carrier.

8. A process for the preparation of a liposome composition comprising selegilin or a pharmaceutically acceptable salt thereof, or mixtures thereof, comprising evaporating an organic solvent from an organic solvent mixture comprising liposoluble components having at least one lipid, and selegilin, and combining with an aqueous solution of one or more water-soluble under stirring.

9. The process according to claim 8, wherein said organic solvent mixture is chloroform and methanol.

10. A method for the treatment of Alzheimer's disease, Parkinson's disease, depression, stroke, motion sickness or myelitis which comprises administering to a patient in need thereof, a liposome composition according to any one of claims 1 or 2.

11. The composition according to claim 7 in oral form.

12. The composition according to claim 7 in parenteral form.

13. The composition according to claim 7 in trandermal form.

14. A composition comprising an admixture (a) at least 10% of selegilin, or a pharmaceutically acceptable salt thereof, or mixtures thereof in a uni- or multilamellar vesicle; and the balance of selegilin outside of said uni- or multilamellar vesicle, in a liquid or solid carrier.

* * * * *